US010294296B2

(12) United States Patent
Simard

(10) Patent No.: US 10,294,296 B2
(45) Date of Patent: May 21, 2019

(54) TREATMENT FOR NEOPLASTIC DISEASES

(75) Inventor: John Simard, Austin, TX (US)

(73) Assignee: XBiotech, Inc., Vancouver (CA)

(*) Notice: Subject to any disclaimer, the term of this patent is extended or adjusted under 35 U.S.C. 154(b) by 1688 days.

(21) Appl. No.: 13/215,464

(22) Filed: Aug. 23, 2011

(65) Prior Publication Data
US 2012/0045444 A1 Feb. 23, 2012

Related U.S. Application Data

(60) Provisional application No. 61/376,097, filed on Aug. 23, 2010, provisional application No. 61/406,759, filed on Oct. 26, 2010, provisional application No. 61/411,183, filed on Nov. 8, 2010, provisional application No. 61/480,635, filed on Apr. 29, 2011.

(51) Int. Cl.
*A61K 39/395* (2006.01)
*C07K 16/24* (2006.01)
*A61K 39/00* (2006.01)

(52) U.S. Cl.
CPC ...... *C07K 16/245* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,634,664 A | 1/1987 | Oestberg | |
| 4,965,198 A | 10/1990 | Yamasaki et al. | |
| 5,034,316 A | 7/1991 | Weisbart et al. | |
| 5,168,062 A | 12/1992 | Stinski | |
| 5,231,024 A | 7/1993 | Moeller et al. | |
| 5,585,089 A | 12/1996 | Queen et al. | |
| 5,654,407 A | 8/1997 | Boyle et al. | |
| 5,693,762 A | 12/1997 | Queen et al. | |
| 5,792,838 A | 8/1998 | Smith et al. | |
| 5,795,967 A | 8/1998 | Aggarwal et al. | |
| 5,932,188 A | 8/1999 | Snow et al. | |
| 5,959,085 A * | 9/1999 | Garrone et al. | 530/387.3 |
| 6,090,382 A | 7/2000 | Salfeld et al. | |
| 6,140,470 A | 10/2000 | Garen et al. | |
| 6,623,736 B2 | 9/2003 | Tobinick | |
| 7,718,674 B2 | 5/2010 | Aberg | |
| 8,398,966 B2 | 3/2013 | Wu | |
| 2003/0026806 A1 | 2/2003 | Witte et al. | |
| 2003/0040617 A9 | 2/2003 | Rosen et al. | |
| 2003/0175832 A1 | 9/2003 | Marton | |
| 2003/0232054 A1 | 12/2003 | Tang et al. | |
| 2004/0097712 A1 | 5/2004 | Varnum | |
| 2004/0185514 A1 | 9/2004 | Frostegard | |
| 2005/0054019 A1 | 3/2005 | Michaud et al. | |
| 2005/0129699 A1 * | 6/2005 | Salcedo et al. | 424/155.1 |
| 2005/0147603 A1 | 7/2005 | Smith et al. | |
| 2005/0276807 A1 | 12/2005 | Skurkovich | |
| 2006/0127407 A1 * | 6/2006 | Chen et al. | 424/178.1 |
| 2006/0159775 A1 | 7/2006 | McGrath | |
| 2007/0071675 A1 | 3/2007 | Wu et al. | |
| 2008/0050310 A1 | 2/2008 | Ebens, Jr. et al. | |
| 2009/0123415 A1 | 5/2009 | Simard | |
| 2009/0191149 A1 | 7/2009 | Simard | |
| 2009/0258070 A1 | 10/2009 | Burnier | |
| 2009/0291081 A1 | 11/2009 | Hsieh | |
| 2009/0298096 A1 | 12/2009 | Simard | |
| 2010/0040574 A1 | 2/2010 | Simard | |
| 2010/0047239 A1 | 2/2010 | Wu | |
| 2010/0221179 A1 | 2/2010 | Hsieh | |
| 2010/0068212 A1 | 3/2010 | Simard | |
| 2011/0008282 A1 | 1/2011 | Simard | |
| 2011/0142761 A1 | 6/2011 | Wu | |
| 2013/0039921 A1 | 2/2013 | Simard | |
| 2013/0078258 A1 | 3/2013 | Simard | |
| 2013/0195877 A1 | 8/2013 | Simard | |
| 2013/0287788 A1 | 10/2013 | Simard | |
| 2014/0086933 A1 | 3/2014 | Simard | |

FOREIGN PATENT DOCUMENTS

| | | |
|---|---|---|
| AU | 2007202323 | 5/2007 |
| EP | 0267611 | 5/1993 |
| EP | 0659766 | 6/1995 |
| WO | 9635719 | 11/1996 |
| WO | 2004100987 | 11/2004 |
| WO | 2007015128 | 2/2007 |
| WO | 2007039552 | 4/2007 |
| WO | 2007120828 | 10/2007 |
| WO | 2007132338 | 11/2007 |
| WO | 2007135546 | 11/2007 |
| WO | 9006371 | 9/2009 |
| WO | 2009148575 | 12/2009 |
| WO | 2010030979 | 3/2010 |
| WO | 2010087972 | 8/2010 |

(Continued)

OTHER PUBLICATIONS

Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.

Yanni, G. et al: "Intramuscular gold decreases cytokine expression and macrophage numbers in the rheumatoid synovial membrane," Annals of the Rheumatic Diseases, 1994, vol. 53:315-322.

Dekker, S.K. et al: "Characterization of interleukin-1alpha-induced melanoma cell motility: inhibition by type I and type II receptor-blocking monoclonal antibodies," Melanoma Research, 1997, vol. 7:223-230.

Kleiman, et al: "Invasion assays," Current Protocols in Cell Biology, 2001, 12.2.1-12.2.5.

Sawai, H. et al: "Interleukin-1alpha enhances the aggressive behavior of pancreatic cancer cells by regulating the alpha 6 beta I-integrin and urokinase plasminogen activator receptor expression," MC Cell Biology, 2006:1-13.

(Continued)

*Primary Examiner* — Michael D Pak
(74) *Attorney, Agent, or Firm* — Stanley A. Kim

(57) ABSTRACT

Administration of a mAb that specifically binds IL-1α is useful for treating tumor-associated diseases in human subjects.

2 Claims, No Drawings

(56) References Cited

FOREIGN PATENT DOCUMENTS

| WO | 2013043973 | 3/2013 |
|---|---|---|
| WO | 2014055541 | 4/2014 |
| WO | 2014055544 | 4/2014 |

OTHER PUBLICATIONS

Lewis, Anne M. et al: "Interleukin-I and cancer progression: the emerging role of interleukin-I receptor antagonist as a novel therapeutic agent in cancer treatment," Journal of Translational Medicine, 2006, vol. 4:1-12.

Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.

Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.

Voronov, E. et al: "IL-1 is required for tumor invasiveness and angiogenesis," PNAS, 2003, vol. 100, No. 5:2645-2650.

Uefuji, K. et al: "Increased expression of interleukin-1alpha and cyclooxygenase-2 in human gastric cancer: a possible role in tumor progression," 2005, Anticancer Research, vol. 25:3225-3230.

Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

Bendtzen, Klaus et al., High-Avidity Autoantibodies to Cytokines, Trends Immunology Today, May 1998, vol. 19, No. 5 209.

Bendtzen, Klaus et al., Detection of Autoantibodies to Cytokines, Molecular Biotechnology, 2000, vol. 14.

Dardik, Alan et al., Shear stress-stimulated endothelial cells induce smooth muscle cell chemotaxis via platelet-derived growth factor-BB and interleukin-1alpha, Journal of Vascular Surgergy, Feb. 2005, vol. 41:321-331.

Dinarello, Charles A., Modalities for reducing interleukin 1 activity in disease, TiPs, May 1993, vol. 14:155-159.

Dinarello, Charles A. et al., Anticytokine strategies in the treatment of the systemic inflammatory response syndrome, The Journal of the American Medical Association, Apr. 1993, vol. 269, No. 14:1829-1835.

Dinarello, Charles A., Biologic basis for interleukin-1 in disease, Blood, Mar. 1996, vol. 87, No. 6:2095-2147.

Dinarello, Charles A., Therapeutic strategies to reduce IL-1 activity in treating local and system inflammation, Current Opinion in Pharmacology, 2004, vol. 4:378-385.

Larrick, James W. et al., Prospects for the therapeutic use of human monoclonal antibodies, Journal of Biological Response Modifiers, 1986, vol. 5:379-393.

Garrone, P. et al., Generation and characterization of a human monoclonal autoantibody that acts as a high affinity interleukin-1alpha specific inhibitor, Molecular Immunology, 1996, vol. 33. No. 78:649-658.

Griffiths, Andrew D. et al., Human anti-self antibodies with high specificity from phage display libraries, the EMBO Journal, 1993, vol. 12, No. 2:725-734.

Satoh, H. et al., Characterization of anti-IL-1alpha autoantibodies in the sera from healthy humans, Immunopharmacology, 1994, vol. 27:107-118.

Hansen, M. B. et al., Sex- and age-dependency of IgG autoantibodies against IL-1alpha in healthy humans, European Journal of Clinical Investigation, 1994, vol. 24:212:218.

Jouvenne, P. et al., High levels of neutralizing autoantibodies against IL-1alpha are associated with a better prognosis in chronic polyarthritis: a follow-up study, Scand. J. Immunol., 1997, vol. 46:413-418.

Lindqvist, E. et al., Prognostic laboratory markers of joint damage in rheumatoid arthritis, Ann Rheum Dis, 2005, vol. 64:196-201.

Ogushi, F. et al., Autoantibodies to IL-1alpha in sera from rapidly progressive idiopathic pulmonary fibrosis, The Journal of Medical Investigation, 2001, vol. 48:181-189.

Ross, Christian, et al., High avidity IFN-neutralizing antibodies in pharmaceutically prepared human IgG, J. Clin. Invest., May 1995, vol. 95:1974-1978.

Saurat, Jean-Hilaire, et al., Anti-interleukin-1alpoha autoantibodies in humans: Characterization, isotype distribution, and receptor-binding inhibition—Higher frequency in Schnitzler's syndrome (urticaria and macroglobulinemia), J. Allergy Clin. Immunol., Aug. 1991, vol. 88, No. 2:243-256.

Suzuki, Hiroshi et al., Demonstration of Neutralizing Autoantibodies against II-1alpha IN sera from patients with rheumatoid arthritis, The Journal of Immunology, Oct. 1, 1990, vol. 145, No. 7:2140-2146.

Svenson, M. et al., IgG Autoantibodies against Interleuking 1alpha in sera of normal individuals, Scand. J. Immunol., 1989, vol. 29:489-492.

Svenson, M. et al., Binding of Cytokines to Pharmaceutically Prepared Human Immunoglobulin, J. Clin. Invest., Nov. 1993, vol. 92:2533-2539.

Svenson, M. et al., Effects of human anti-IL-1alpha autoantibodies on receptor binding and biological activities of IL-1 alpha, Cytokine, Mar. 1992, vol. 4, No. 2:125-133.

Svenson, M. et al., Distribution and characterization of autoantibodies to interleukin 1 alpha in normal human sera, Scand. J. Immunol., 1990, vol. 32:695-701.

Svenson, M. et al., Antibody to granulocyte-macrophage colony-stimulating factor is a dominant anti-cytokine activity in human IgG preparations, Blood, Mar. 1998, vol. 91, No. 6:2054-2061.

Svenson, M. et al., Cytokine vaccination: neutralising IL-1alpha autoantibodies induced by immunisation with homologous IL-1alpha, Journal of immunological methods, 2000:1-8.

Waehre et al., Increased expression of interleukin-1 in coronary artery disease with downregulatory effects of HMG-CoA reductase inhibitors, «circ.ahajournals.org», downloaded on Jan. 15, 2008:1966-1972.

Clinton Steven K. et al., Interleukin-1 gene expression in rabbit vascular tissue in vivo, American Journal of Pathology, Apr. 1991, vol. 138, No. 4:1005-1014.

Von Der Thusen, Jan H., et al., Interleukins in atherosclerosis: Molecular pathways and therapeutic potential, Pharmacol Rev, 2003, vol. 55, No. 1:133-166.

Kasahara, T. et al., Preparation and characterization of polyclonal and monoclonal antibodies against human interleukin 1 alpha (IL 1alpha), The Journal of Immunology, Mar. 1987, vol. 138, No. 6:1804-1812.

Merhi-Soussi, F. et al., Interleukin-1 plays a major role in vascular inflammation and atherosclerosis in male apoliprotein E-knockout mice, Cardiovacular Research, 2006, vol. 66:583-593.

Ross, C. et al., Increased in vivo antibody activity against interferon alpha, interleuking-1alpha, and interleukin-6 after high-dose Ig therapy, Blood, Sep. 1997, vol. 90, No. 6:2376-2380.

Ito, R. et al., Interleukin 1alpha acts as an autocrine growth stimulator for human gastric carcinoma cells, Cancer Research, Sep. 1993, vol. 53:4102-4106.

Shirakawa, F. et al., Autocrine stimulation of interleukin 1alpha in the growth of adult human T-cell leukemia cells, Cancer Rsearch, March, 1089, vol. 49:1143-1147.

Apte, Ron N., et al., Effects of micro-environment- and malignant cell-derived interleukin-1 in carcinogenesis, tumour invasiveness and tumour-host interactions, European Journal of Cancer, 2006, vol. 42:751-759.

Dinarello, Charles A., The role of interleukin-1 in disease, The New England Journal of Medicine, 1993, vol. 328, No. 2:106-113.

Wake, R. et al., Gender differences in ischemic heart disease, Recent Patents on Cardiovascular Drug Discovery, 2009, vol. 4:234-240.

Mariotti, Massimo et al., Interleukin 1 alpha is a marker of endothelial cellular senescent, Immunity & Ageing, Apr. 2006:1-6.

Niki, Yasuo et al., Membrane-associated IL-1 contributes to Chronic Synovitis and cartilage destruction in human IL-1alpha transgenic mice, The Journal of Immunology, 2004:577-584.

(56) References Cited

OTHER PUBLICATIONS

McHale, Julie F. et al., TNF-alpha and IL-sequentially induce endothelial ICAM-1 and VCAM-1 expression in MRL/Ipr lupus-prone mice, The American Association of Immunologists, 1999, vol. 163:3993-4000.
Sandborg, Christy L. et al., Modulation of IL-1alpha, IL-1beta, and 25K Mr Non-IL-1 activity released by human mononuclear cells, Journal of Leukocyte Biology, 1989, vol. 46:417-427.
GenBank entry AY510107.1, *Homo sapiens* 9F11 monoclonal IgM antibody light chain mRNA, complete cds, 2005 (retrieved from the Internet on Apr. 23, 2010, <http://www.ncbi.nlm.nih.gov/nuccore/41388185>.
Sunahara, N. et al., Differential determination of recombinant hum interleukin-1 alpha and its deamidated derivative by two sandwhich enzyme immunoassays using monoclonal antibodies. Comparison with a polyclonal antibody-based competitive enzyme immunoassay., J Immunol Methods, 1989, vol. 119:75-82 (Abstract only).
Miossec, P., Anti-interleukin 1alpha autoantibodies, Ann Rheum Dis, 2022, vol. 61:577-579.
Horai, R. et al., Production of mice deficient in genes for interleukin (IL)-1alpha, IL-1beta, IL-1alpha/beta, and IL-1 receptor antagonist shows that IL-1beta is crucial in turpentine-induced fever development and glucocorticoid secretion, J. Exp. Med, 1998, vol. 187, No. 9:1463-1475.
Kanai, T. et al., Extracorporeal elimination of TNF-alpha-producing CD14 dull CD16+ monocytes in leukocytapheresis therapy for ulcerative colitis, Inflamm Bowel Dis, Mar. 2007, vol. 13, No. 3:284-290.
Braddock, M. et al., Therapeutic potential of targeting IL-1 and IL-18 in inflammation, Expert Opin. Biol. Ther., 2004, vol. 4, No. 6:8476-860.
Eugui, E.M. et al., Antibodies against membrane interleukin 1alpha activate accessory cells to stimulate proliferation of T lymphocytes, Proc. Natl. Acad. Sci USA, 1990, vol. 87:1305-1309.
Janeway, C.A., Jr. et al, The induction, measurement, and manipulation of the immune response, ImmunoBiology, the Immune System in Health and Disease, 1997, Third Edition.
Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.
Jefferis, Roy: "Antibody therapeutics: isotype and glycoform selection," Expert Opin. Biol. Ther. (2007) 7 (9):1401-1413.
Salfeld, J.G.: "Isotype selection in antibody engineering," Nature Biotechnology (2007), vol. 25, No. 12:1369-1372.
Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.
Buchan, G. et al: "Interleukin-1 and tumour necrosis factor mRNA expression in rheumatoid arthritis: prolonged production of IL-1alpha," Clin. Exp. Immunol. (1988), vol. 73:449-455.
Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.
Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.
Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.

Chamberlain, R.S. et al., Innovations and strategies for the development of anticancer vaccines, Exp. Opin. Pharmacother., 2000, vol. 1(4)603-614.
Janik, John E. et al: "Interleukin 1alpha increases serum leptin concentrations in humans," Journal of Clinical Endocrinology and Metabolism, vol. 92, No. 9, 1997: 3084-3086.
Kurokawa, Ichiro et al: "New developments in our understanding of acne pathogenesis and treatment," Experimental Dermatology, vol. 18, 2009:821-832.
Lubberts, Erik, et al: "Treatment with a neutralizing anti-murine inerleukin-17 antibody after the onset of collagen-induced arthritis reduces joint inflammation, cartilage destruction, and bone erosion," Arthritis & Rheumatism, vol. 50, No. 2, Feb. 2004:650-659.
Oriuchi, Noboru et al: "Current status of cancer therapy with radiolabeled monoclonal antibody," Annals of Nuclear Medicine, vol. 19, No. 5, 2005:355-365.
Boselli, Joseph et al: Fibronectin: Its relationshp to basement membranes, Light Microscopic Studies, Cell.Res., vol. 5, 1981:391-404.
Clinical Trial Review: Acne; «http://jddonline.com/articles/dermatology/S1545961612P0780X/1», last visited on Oct. 16, 2014.
Hoge, E.A. et al: "Broad spectrum of cytokine abnormalities in panic disorder and posttraumatic stress disorder," Depression and Anxiety, vol. 26, No. 5, May 2009:447-455; Abstract only.
Mach, Francois: "Toward new therapeutic strategies against neointimal formation in restenosis," Arterioscler Thromb Vasc Biol, vol. 20, 2000:1699-1700.
Morton, Allison, C. et al: "Interleukin-1 receptor antagonist alters the response to vessel wall injury in a porcine coronary artery model," Cardiovascular Research, vol. 68, 2005: 493-501.
Heyderman, R.S. et al: "Modulation of the endothelial procoagulant response to lipoploysaccharide and tumour necrosis factor-alpha in-vitro: The effects of dexamethasone, pentoxifylline, iloprost and a polyclonal anti-human IL-1alpha antibody, " Inflamm Res, vol. 44, 1995:275-280.
Joosten, M. et al: "Amelioration of established collagen-induced arthritis (CIA) with anti-IL-1," Agents Actions. vol. 41, Special Conference Issue, 1994:C174-C176.
U.S. National Institutes of Health: "Safety and Preliminary Efficacy Study of an Anti-inflammatory Therapeutic Antibody in Reducing Restenosis," NCT01270945, ClinicalTrials.gov, Jan. 4, 2011.
XBiotech, Inc. Pressrelease: "XBiotech Files Investigational New Drug (IND) Application with the FDA for the treatment of Chronic Myelogenous Leukemia," Evaluate, Nov. 22, 2010.
Rhim, JH, et al.: "Cancer cell-derived IL-1alpha induces II-8 release in endothelial cells," J Cancer Res Clin Oncol, Jan. 2008, vol. 134(1):45-50. Epub Jul. 11, 2007; (Abstract only).
Sakurai, T. et al.: "Hepatocyte Necrosis Induced by Oxidative Stress and IL-1alpha Release Mediate Carcinogen-Induced Compensatory Proliferation and Liver Tumorigenesis," Cancer Cell, Aug. 12, 2008, vol. 14:156-165.
Mizutani, H.: "Endogenous neutralizing anti-II-1alpha antibodies in inflammatory skin diseases: possible natural inhibitor for over expressed epidermal IL-1," 1999, Journal of Dermatological Science, vol. 20:63-71.
Zhu, Y. et al., "The clinical study about interleukin-1 and tumor necrosis factor alpha in hepatocirrhosis," Chinese Journal of Clinical Hepatology, 2001, vol. 17, Issue 4: 233-234.
Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.

\* cited by examiner

TREATMENT FOR NEOPLASTIC DISEASES

CROSS-REFERENCE TO RELATED APPLICATIONS

The present application claims the priority of U.S. provisional patent application Ser. Nos. 61/376,097 filed on Aug. 23, 2010, 61/406,759 filed on Oct. 26, 2010, 61/411,183 filed on Nov. 8, 2010, and 61/480,635 filed on Apr. 29, 2011, all of which are incorporated herein by reference in their entirety.

STATEMENT AS TO FEDERALLY SPONSORED RESEARCH

Not applicable.

FIELD OF THE INVENTION

The invention relates generally to the fields of medicine, oncology, and immunology. More particularly, the invention relates to the use of antibodies (Abs) which specifically bind interleukin-1α (IL-1α) to treat a tumor-associated disease and other tumor-associated pathologies.

BACKGROUND

Despite many advances, tumor-associated diseases such as cancer remain one of the leading causes of death and morbidity in developed nations. Although many of the molecular mechanisms of tumorigenesis have now been revealed, standard treatment of most aggressive tumors continues to be surgical resection, chemotherapy, and radiotherapy. While increasingly successful, each of these treatments still causes numerous undesired side effects. For example, surgery results in pain, traumatic injury to healthy tissue, and scarring. Radiotherapy and chemotherapy cause nausea, immune suppression, gastric ulceration, and secondary tumorigenesis.

Over the last several years much progress has been made using biologic agents such as Abs to treat cancerous tumors. Abs can directly target specific types of tumor cells to harness a patient's immune response to kill the tumor. Alternatively, they can target cell growth factors to interfere with the growth of tumor cells. As with conventional chemotherapeutic agents, not all anti-tumor Abs are useful for treating all types of neoplasms, and many initially effective antibodies later lose potency. Thus new anti-tumor Abs are needed.

SUMMARY

The invention is based on the discovery that a mAb that specifically binds IL-1α is useful for treating various tumor-associated diseases.

Accordingly, the invention features a medicament and method for treating neoplastic diseases (e.g., a colorectal cancer such as one having a KRAS mutation, an EBV-associated cancer such as nasopharygeal carcinoma or Burkitt's lymphoma, non-small cell lung cancer (NSCLC) or non-cancerous conditions associated with tumors such as Castleman's disease) in a human subject. The method can be performed by administering to the subject a pharmaceutical composition including a pharmaceutically acceptable carrier and an amount of an anti-IL-1α Ab effective to ameliorate a symptom of a tumor-associated pathology and/or to reduce the size of a tumor in the subject by at least about 10% (e.g., at least 8, 9, 10, 15, 17, 20, 30, 40, 50, 60, 70, 80, 90, or 100%). The medicament can include an anti-IL-1α Ab. The anti-IL-1α Ab can be a mAb such as an IgG1. The anti-IL-1α Ab can be the mAb designated as MABp1 or a mAb that includes one or more complementarity determining regions (CDRs) of MABp1.

The pharmaceutical composition can be administered to the subject by injection, subcutaneously, intravenously, intramuscularly, or directly into a tumor. In the method, the dose can be at least 0.25 (e.g., at least 0.2, 0.5, 0.75, 1, 2, 3, 4, or 5) mg/ml.

Unless otherwise defined, all technical terms used herein have the same meaning as commonly understood by one of ordinary skill in the art to which this invention belongs. Commonly understood definitions of biological terms can be found in Rieger et al., Glossary of Genetics: Classical and Molecular, 5th edition, Springer-Verlag: New York, 1991; and Lewin, Genes V, Oxford University Press: New York, 1994. Commonly understood definitions of medical terms can be found in Stedman's Medical Dictionary, 27$^{th}$ Edition, Lippincott, Williams & Wilkins, 2000.

As used herein, an "Ab" or "Ab" is an immunoglobulin (Ig), a solution of identical or heterogeneous Igs, or a mixture of Igs. An "Ab" can also refer to fragments and engineered versions of Igs such as Fab, Fab', and F(ab')$_2$ fragments; and scFv's, heteroconjugate Abs, and similar artificial molecules that employ Ig-derived CDRs to impart antigen specificity. A "mAb" or "mAb" is an Ab expressed by one clonal B cell line or a population of Ab molecules that contains only one species of an antigen binding site capable of immunoreacting with a particular epitope of a particular antigen. A "polyclonal Ab" or "polyclonal Ab" is a mixture of heterogeneous Abs. Typically, a polyclonal Ab will include myriad different Ab molecules which bind a particular antigen with at least some of the different Abs immunoreacting with a different epitope of the antigen. As used herein, a polyclonal Ab can be a mixture of two or more mAbs.

An "antigen-binding portion" of an Ab is contained within the variable region of the Fab portion of an Ab and is the portion of the Ab that confers antigen specificity to the Ab (i.e., typically the three-dimensional pocket formed by the CDRs of the heavy and light chains of the Ab). A "Fab portion" or "Fab region" is the proteolytic fragment of a papain-digested Ig that contains the antigen-binding portion of that Ig. A "non-Fab portion" is that portion of an Ab not within the Fab portion, e.g., an "Fc portion" or "Fc region." A "constant region" of an Ab is that portion of the Ab outside of the variable region. Generally encompassed within the constant region is the "effector portion" of an Ab, which is the portion of an Ab that is responsible for binding other immune system components that facilitate the immune response. Thus, for example, the site on an Ab that binds complement components or Fc receptors (not via its antigen-binding portion) is an effector portion of that Ab.

When referring to a protein molecule such as an Ab, "purified" means separated from components that naturally accompany such molecules. Typically, an Ab or protein is purified when it is at least about 10% (e.g., 9%, 10%, 20%, 30% 40%, 50%, 60%, 70%, 80%, 90%, 95%, 98%, 99%, 99.9%, and 100%), by weight, free from the non-Ab proteins or other naturally-occurring organic molecules with which it is naturally associated. Purity can be measured by any appropriate method, e.g., column chromatography, polyacrylamide gel electrophoresis, or HPLC analysis. A chemically-synthesized protein or other recombinant protein produced in a cell type other than the cell type in which it naturally occurs is "purified."

By "bind", "binds", or "reacts with" is meant that one molecule recognizes and adheres to a particular second molecule in a sample, but does not substantially recognize or adhere to other molecules in the sample. Generally, an Ab that "specifically binds" another molecule has a $K_d$ greater than about $10^5$, $10^6$, $10^7$, $10^8$, $10^9$, $10^{10}$, $10^{11}$, or $10^{12}$ liters/mole for that other molecule.

A "therapeutically effective amount" is an amount which is capable of producing a medically desirable effect in a treated animal or human (e.g., amelioration or prevention of a disease or symptom of a disease).

Although methods and materials similar or equivalent to those described herein can be used in the practice or testing of the present invention, suitable methods and materials are described below. All publications mentioned herein are incorporated by reference in their entirety. In the case of conflict, the present specification, including definitions will control. In addition, the particular embodiments discussed below are illustrative only and not intended to be limiting.

DETAILED DESCRIPTION

The invention encompasses compositions and methods for ameliorating one or more symptoms of a tumor-associated pathology in a subject. The below described preferred embodiments illustrate adaptation of these compositions and methods. Nonetheless, from the description of these embodiments, other aspects of the invention can be made and/or practiced based on the description provided below.

General Methodology

Methods involving conventional immunological and molecular biological techniques are described herein Immunological methods (for example, assays for detection and localization of antigen-Ab complexes, immunoprecipitation, immunoblotting, and the like) are generally known in the art and described in methodology treatises such as Current Protocols in Immunology, Coligan et al., ed., John Wiley & Sons, New York. Techniques of molecular biology are described in detail in treatises such as Molecular Cloning: A Laboratory Manual, 2nd ed., vol. 1-3, Sambrook et al., ed., Cold Spring Harbor Laboratory Press, Cold Spring Harbor, N.Y., 2001; and Current Protocols in Molecular Biology, Ausubel et al., ed., Greene Publishing and Wiley-Interscience, New York. Ab methods are described in Handbook of Therapeutic Abs, Dubel, S., ed., Wiley-VCH, 2007. General methods of medical treatment are described in McPhee and Papadakis, Current Medical Diagnosis and Treatment 2010, 49$^{th}$ Edition, McGraw-Hill Medical, 2010; and Fauci et al., Harrison's Principles of Internal Medicine, 17$^{th}$ Edition, McGraw-Hill Professional, 2008

Treatment of a Tumor-Associated Disease

The compositions and methods described herein are useful for treating a tumor-associated disease in a mammalian subject by administering to the subject a pharmaceutical composition including an amount of an anti-IL-1α Ab effective to improve at least one characteristic of the tumor-associated disease in the subject. The mammalian subject might be any that suffers from a tumor-associated disease including, human beings, dogs, cats, horses, cattle, sheep, goats, and pigs. Human subjects might be male, female, adults, children, seniors (65 and older), and those with other diseases. Particularly preferred subjects are those whose disease has progressed after treatment with chemotherapy, radiotherapy, surgery, and/or biologic agents. Any type of a tumor-associated disease susceptible to treatment with an anti-IL-1α Ab might be targeted. Anti-IL-1α Ab administration is thought to be particularly effective for treating colorectal tumors (e.g., colorectal cancers with a KRAS mutation), EBV-associated neoplasms such as nasopharyngeal cancer or Burkitt's lymphoma, NSCLC, and blood cell neoplasms such as in Castleman's disease. A disease with tumors expressing IL-1α or tumors infiltrated with IL-1α inflammatory cells might also be targeted. The particular characteristic of a tumor-associated disease to be improved can be tumor size (e.g., T0, T is, or T1-4), state of metastasis (e.g., M0, M1), number of observable tumors, node involvement (e.g., N0, N1-4, Nx), grade (i.e., grades 1, 2, 3, or 4), stage (e.g., 0, I, II, III, or IV), presence or concentration of certain markers on the cells or in bodily fluids (e.g., AFP, B2M, beta-HCG, BTA, CA 15-3, CA 27.29, CA 125, CA 72.4, CA 19-9, calcitonin, CEA, chromgrainin A, EGFR, hormone receptors, HER2, HCG, immunoglobulins, NSE, NMP22, PSA, PAP, PSMA, S-100, TA-90, and thyroglobulin), and/or associated pathologies (e.g., ascites or edema) or symptoms (e.g., cachexia, fever, anorexia, or pain). The improvement, if measureable by percent, can be at least 5, 10, 15, 20, 25, 30, 40, 50, 60, 70, 80, or 90% (e.g., volume or linear dimensions of a tumor).

Antibodies and Other Agents that Target IL-1α

Any suitable type of Ab or other biologic agent (e.g., a fusion protein including an IL-1α-binding component such as an IL-1 receptor) that specifically binds IL-1α and reduces a characteristic of a tumor-associated disease in a subject might be used in the invention. For example, the anti-IL-1α Ab used might be mAb, a polyclonal Ab, a mixture of mAbs, or an Ab fragment or engineered Ab-like molecule such as an scFv. The Ka of the Ab is preferably at least $1 \times 10^9$ M$^{-1}$ or greater (e.g., greater than $9 \times 10^{10}$ M$^{-1}$, $8 \times 10^{10}$ M$^{-1}$, $7 \times 10^{10}$ M$^{-1}$, $6 \times 10^{10}$ M$^{-1}$, $5 \times 10^{10}$ M$^{-1}$, $4 \times 10^{10}$ M$^{-1}$, $3 \times 10^{10}$ M$^{-1}$, $2 \times 10^{10}$ M$^{-1}$, or $1 \times 10^{10}$ M$^{-1}$). In a preferred embodiment, the invention utilizes a fully human mAb that includes (i) an antigen-binding variable region that exhibits very high binding affinity (e.g., at least nano or picomolar) for human IL-1α and (ii) a constant region. The human Ab is preferably an IgG1, although it might be of a different isotype such as IgM, IgA, or IgE, or subclass such as IgG2, IgG3, or IgG4. One example of a particularly useful mAb is MABp1, an IL-1α-specific IgG1 mAb described in U.S. patent application Ser. No. 12/455,458 filed on Jun. 1, 2009. Other useful mAbs are those that include at least one but preferably all the CDRs of MABp1.

Because B lymphocytes which express Ig specific for human IL-1α occur naturally in human beings, a presently preferred method for raising mAbs is to first isolate such a B lymphocyte from a subject and then immortalize it so that it can be continuously replicated in culture. Subjects lacking large numbers of naturally occurring B lymphocytes which express Ig specific for human IL-1α may be immunized with one or more human IL-1α antigens to increase the number of such B lymphocytes. Human mAbs are prepared by immortalizing a human Ab secreting cell (e.g., a human plasma cell). See, e.g., U.S. Pat. No. 4,634,664.

In an exemplary method, one or more (e.g., 5, 10, 25, 50, 100, 1000, or more) human subjects are screened for the presence of such human IL-1α-specific Ab in their blood. Those subjects that express the desired Ab can then be used as B lymphocyte donors. In one possible method, peripheral blood is obtained from a human donor that possesses B lymphocytes that express human IL-1α-specific Ab. Such B lymphocytes are then isolated from the blood sample, e.g., by cells sorting (e.g., fluorescence activated cell sorting, "PACS"; or magnetic bead cell sorting) to select B lymphocytes expressing human IL-1α-specific Ig. These cells can then be immortalized by viral transformation (e.g., using EBV) or by fusion to another immortalized cell such as a human myeloma according to known techniques. The B lymphocytes within this population that express Ig specific for human IL-1α can then be isolated by limiting dilution methods (e.g., cells in wells of a microtiter plate that are positive for Ig specific for human IL-1α are selected and subcultured, and the process repeated until a desired clonal line can be isolated). See, e.g., Goding, MAbs: Principles and Practice, pp. 59-103, Academic Press, 1986. Those clonal cell lines that express Ig having at least nanomolar or picomolar binding affinities for human IL-1α are preferred. MAbs secreted by these clonal cell lines can be purified from the culture medium or a bodily fluid (e.g., ascites) by conventional Ig purification procedures such as salt cuts, size exclusion, ion exchange separation, and affinity chromatography.

Although immortalized B lymphocytes might be used in in vitro cultures to directly produce mAbs, in certain cases it might be desirable to use heterologous expression systems to produce mAbs. See, e.g., the methods described in U.S. patent application Ser. No. 11/754,899. For example, the genes encoding an mAb specific for human IL-1α might be cloned and introduced into an expression vector (e.g., a plasmid-based expression vector) for expression in a heterologous host cell (e.g., CHO cells, COS cells, myeloma cells, and E. coli cells). Because Igs include heavy (H) and light (L) chains in an $H_2L_2$ configuration, the genes encoding each may be separately isolated and expressed in different vectors.

Although generally less preferred due to the greater likelihood that a subject will develop an anti-Ab response, chimeric mAbs (e.g., "humanized" mAbs), which are antigen-binding molecules having different portions derived from different animal species (e.g., variable region of a mouse Ig fused to the constant region of a human Ig), might be used in the invention. Such chimeric Abs can be prepared by methods known in the art. See, e.g., Morrison et al., Proc. Nat'l. Acad. Sci. USA, 81:6851, 1984; Neuberger et al., Nature, 312:604, 1984; Takeda et al., Nature, 314:452, 1984. Similarly, Abs can be humanized by methods known in the art. For example, mAbs with a desired binding specificity can be humanized by various vendors or as described in U.S. Pat. Nos. 5,693,762; 5,530,101; or 5,585,089.

The mAbs described herein might be affinity matured to enhance or otherwise alter their binding specificity by known methods such as VH and VL domain shuffling (Marks et al. Bio/Technology 10:779-783, 1992), random mutagenesis of the hypervariable regions (HVRs) and/or framework residues (Barbas et al. Proc Nat. Acad. Sci. USA 91:3809-3813, 1994; Schier et al. Gene 169:147-155, 1995; Yelton et al. J. Immunol. 155:1994-2004, 1995; Jackson et al., J. Immunol. 154(7):3310-9, 1995; and Hawkins et al, J. Mol. Biol. 226:889-896, 1992. Amino acid sequence variants of an Ab may be prepared by introducing appropriate changes into the nucleotide sequence encoding the Ab. In addition, modifications to nucleic acid sequences encoding mAbs might be altered (e.g., without changing the amino acid sequence of the mAb) for enhancing production of the mAb in certain expression systems (e.g., intron elimination and/or codon optimization for a given expression system). The mAbs described herein can also be modified by conjugation to another protein (e.g., another mAb) or non-protein molecule. For example, a mAb might be conjugated to a water soluble polymer such as polyethylene glycol or a carbon nanotube (See, e.g., Kam et al., Proc. Natl. Acad. Sci. USA 102: 11600-11605, 2005). See, U.S. patent application Ser. No. 11/754,899.

Preferably, to ensure that high titers of human IL-1α-specific mAb can be administered to a subject with minimal adverse effects, the mAb compositions of the invention are at least 0.5, 1, 2, 3, 4, 5, 6, 7, 8, 9, 10, 11, 12, 13, 14, 15, 20, 25, 30, 35, 40, 45, 50, 60, 70, 80, 90, 95, 96, 97, 98, 99, 99.9 or more percent by weight pure (excluding any excipients). The mAb compositions of the invention might include only a single type of mAb (i.e., one produced from a single clonal B lymphocyte line) or might include a mixture of two or more (e.g., 2, 3, 4, 5, 6, 7, 8, 9, 10 or more) different types of mAbs.

To modify or enhance their function, the human IL-1α mAbs might be conjugated with another molecule such as a cytotoxin. A human IL-1α specific mAb might be conjugated with one or more cytotoxins to more effectively kill cells expressing IL-1α. Cytotoxins for use in the invention can be any cytotoxic agent (e.g., molecule that can kill a cell after contacting the cell) that can be conjugated to a human IL-1α specific mAb. Examples of cytotoxins include, without limitation, radionuclides (e.g., $^{35}S$, $^{14}C$, $^{32}P$, $^{125}I$, $^{131}I$, $^{90}Y$, $^{89}Zr$, $^{201}Tl$, $^{186}Re$, $^{188}Re$, $^{57}Cu$, $^{213}Bi$, and $^{211}At$), conjugated radionuclides, and chemotherapeutic agents. Further examples of cytotoxins include, but are not limited to, antimetabolites (e.g., 5-fluorouricil (5-FU), methotrexate (MTX), fludarabine, etc.), anti-microtubule agents (e.g., vincristine, vinblastine, colchicine, taxanes (such as paclitaxel and docetaxel), etc.), alkylating agents (e.g., cyclophasphamide, melphalan, bischloroethylnitrosurea (BCNU), etc.), platinum agents (e.g., cisplatin (also termed cDDP), carboplatin, oxaliplatin, JM-216, CI-973, etc.), anthracyclines (e.g., doxorubicin, daunorubicin, etc.), antibiotic agents (e.g., mitomycin-C), topoisomerase inhibitors (e.g., etoposide, tenoposide, and camptothecins), or other cytotoxic agents such as ricin, diptheria toxin (DT), *Pseudomonas* exotoxin (PE) A, PE40, abrin, saporin, pokeweed viral protein, ethidium bromide, glucocorticoid, anthrax toxin and others. See, e.g., U.S. Pat. No. 5,932,188.

While the IL-1α specific Abs described above are preferred for use in the invention, in some cases, other agents that specifically target IL-1α might be used so long as their administration leads to improvement of a characteristic of a tumor-associated disease. These other agents might include small organic molecules, aptamers, peptides, and proteins that specifically bind IL-1α (e.g., anakinra or rilonacept).

Pharmaceutical Compositions and Methods

The anti-IL-1α Ab compositions may be administered to animals or humans in pharmaceutically acceptable carriers (e.g., sterile saline), that are selected on the basis of mode and route of administration and standard pharmaceutical practice. A list of pharmaceutically acceptable carriers, as well as pharmaceutical formulations, can be found in Remington's Pharmaceutical Sciences, a standard text in this field, and in USP/NF. Other substances may be added to the compositions and other steps taken to stabilize and/or preserve the compositions, and/or to facilitate their administration to a subject.

For example, the Ab compositions might be lyophilized (see Draber et al., J. Immunol. Methods. 181:37, 1995; and PCT/US90/01383); dissolved in a solution including sodium and chloride ions; dissolved in a solution including one or more stabilizing agents such as albumin, glucose, maltose, sucrose, sorbitol, polyethylene glycol, and glycine; filtered (e.g., using a 0.45 and/or 0.2 micron filter); contacted with beta-propiolactone; and/or dissolved in a solution including a microbicide (e.g., a detergent, an organic solvent, and a mixture of a detergent and organic solvent.

The Ab compositions may be administered to animals or humans by any suitable technique. Typically, such administration will be parenteral (e.g., intravenous, subcutaneous, intramuscular, or intraperitoneal introduction). The compositions may also be administered directly to the target site (e.g., intratumorally) by, for example, injection. Other methods of delivery, e.g., liposomal delivery or diffusion from a device impregnated with the composition, are known in the art. The composition may be administered in a single bolus, multiple injections, or by continuous infusion (e.g., intravenously or by peritoneal dialysis).

A therapeutically effective amount is an amount which is capable of producing a medically desirable result in a treated animal or human. An effective amount of anti-IL-1α Ab compositions is an amount which shows clinical efficacy in patients as measured by the improvement in one or more a tumor-associated disease characteristics described above. As is well known in the medical arts, dosage for any one animal or human depends on many factors, including the subject's size, body surface area, age, the particular composition to be administered, sex, time and route of administration, general health, and other drugs being administered concurrently. Preferred doses range from about 0.2 to 20 (e.g., 0.15, 0.2, 0.3, 0.4, 0.5, 1, 2, 3, 4, 5, 6, 7, 8, 9, 10, 15, 20, 30, 50, or 100) mg/kg body weight. The dose may be given repeatedly, e.g., hourly, daily, semi-weekly, weekly, bi-weekly, tri-weekly, or monthly.

EXAMPLES

Example 1—Xilonix™

Xilonix™ is a sterile injectable liquid formulation of 15 mg/mL MABp1 in a stabilizing isotonic buffer (pH 6.4). Each 10-mL Type I borosilicate glass serum vial contains 5 mL of the formulation, and is sealed with a 20-mm Dalkyo Fluorotec butyl rubber stopper and flip-off aluminum seal. The product is stored at 5±3° C., with excursions to room temperature permitted. The exact composition of the drug product is shown below:

Composition of the Drug Product (Xilonix™)

| Ingredient | Grade | Manufacturer | Concentration |
| --- | --- | --- | --- |
| MABp1 Ab | GMP | XBiotech | 15 mg/mL |
| sodium phosphate dibasic | compendial | J T Baker | 12 mg/mL |
| citric acid monohydrate | compendial | J T Baker | 2 mg/mL |
| Trehalose.2H2O (high-purity low endotoxin) | compendial | Ferro-Pfanstiehl | 60 mg/mL |
| polysorbate 80 | compendial | J T Baker | 0.2 mg/mL |
| Phosphoric acid, to adjust pH | compendial | J T Baker | 0.04 mg/mL |
| water for injection | compendial | Microbix | q.s. |

Method of Administration:

The calculated volume is withdrawn from the drug (mAb)-containing vial(s) using a suitable syringe. The drug is then injected into a small IV bag containing 100 mL of normal saline (0.9% NaCl) and mixed by inversion. The diluted drug product can be stored at room temperature for 3 hours prior to administration and is infused over a 1-hour period, with the subject being monitored for signs of an infusion reaction. The infusion is chased with a minimum of 30 mLs of normal saline to deliver any product that may be held up in the infusion set.

Example 2—Treatment of Colorectal Cancer with an IL-1α-Specific MAb (Xilonix™)

The human subject was a 63 year-old female diagnosed with metastatic colorectal cancer (KRAS mutation positive). Prior to treatment with Xilonix™, the subject underwent right hemicolectomy and was reportedly staged T3N1MX. She thereafter received adjuvant chemotherapy with FOL-FOX for a total of 12 cycles over about six months. A PET CT scan performed about two months after completion of FOLFOX revealed a mass in her pelvis. The subject was hospitalized at the time for placement of ureteral stent due to obstructive hydronephrosis apparently from the tumor. She started FOLFIR1 and Avastin shortly thereafter and received 8 cycles of therapy. The subject then underwent re-staging PET CT scan which confirmed disease in the pelvis, and also revealed small pulmonary nodules consistent with metastatic disease. A CT scan of the chest, abdomen and pelvis revealed a 12 cm pelvic mass, a 2 cm omental mass, and the hydronephrosis on the right side with associated ureteral stent. She received 2 extra cycles of FOLFIR1 and Avastin. A subsequent PET CT scan showed progression of the bilateral pulmonary nodules. The subject then started irinotecan and Erbitux® (Cetuximab) therapy. A follow up PET CT scan demonstrated disease progression in the lungs.

The subject was initiated on a phase 1 trial with Doxil® (Doxorubicin Liposomal), Velcade® (Bortezomib), and Gemzar® (Gemcitabine) but unfortunately the first re-staging suggested disease progression. She also completed another phase 1 trial with oxaliplatin in combination with azacitydineon and completed 2 cycles before disease progression. At the conclusion of her participation on this last clinical phase 1 trial, the subject was enrolled in the current clinical trial.

She was enrolled in the first dosing cohort (0.25 mg/ml) and completed 5-21 day cycles on the protocol, thus receiving a total of five infusions of MABp1 (0.25 mg/kg) every 21 days. The subject's dose was increased to 0.75 mg/kg on Cycle 6 Day 1. An initial PET CT scan revealed about a 17% reduction in the sum of diameters in the patient's tumors that were being tracked. Following additional doses of MABp1, an over 30% reduction in the sum of diameters in the patient's tracked tumors was observed. A Chest CT showed a paratrocheal lymph node that previously measured 3.5 cm was reduced to 2.9 cm at the end of Cycle 6. A left lung metastasis decreased from 2.2 cm to 1.9 cm, and an implant from the left rectus muscle decreased from 3.2 cm to 2.7 cm. The CEA tumor marker at baseline was 81, decreased to 69.2 at the end of cycle 3, and was 27.9 as of Cycle 7 Day 1. This patient has continued on therapy for over 71 weeks and the disease has remained stable.

Example 3—Treatment of Nasophargeal Cancer with an IL-1α-Specific MAb (Xilonix™)

The subject was a 47 year old Chinese male having EBV+(Epstein-Barr virus) nasopharyngeal carcinoma with the histological subtype lymphoepithelioma (old terminology) or non-keratinizing carcinoma. The subject was previously treated with cisplatin, 5-FU, radiotherapy, Taxotere® (Docetaxel), Gemzar® (Gemcitabine), Xeloda® (Capecitabine), adoptive EBV-directed T cell transfer, and Cymevene® (Ganciclovir) in combination with Gemzar® (Gemcitabine). Prior to starting therapy, the patient had fatigue, fevers and sweats, and was receiving frequent therapeutic paracentesis for ascites.

The subject began MABp1 treatment on day 0 at 1.25 mg/kg IV every two weeks. By days 3 and 4, a marked decrease in the subjects fatigue, fevers, and sweats was noted. The ascites also resolved. Abdominal CT abdomen scans showed a reduction in the size of a metastatic liver tumor from 50.4 mm on day 1 to 35.8 mm by day 36 (almost 30%) of one of the masses. Multiple other liver lesions decreased in size, and bone lesions appeared to be stable.

Example 4—Treatment of Castleman's Syndrome with an IL-1α-Specific MAb (Xilonix™)

The subject was a 55-year-old woman suffering from Castleman's disease (the variant known as POEMS syndrome). Her symptoms included fatigue, edema, and nerve pain. Prior treatment with Rituxan® (Rituximab) and an investigational anti-IL-6 therapy failed. The subject was administered a total of four infusions of MABp1 (0.75 mg/kg) every 21 days. The subject's dose was increased to 1.25 mg/kg in the next cycle.

This subject had stable disease through 2 re-stagings, and has been treated for over 4 months. For approximately 2 weeks after each injection, her symptoms of fatigue, edema, and nerve pain improved significantly, and then gradually recurred until the next injection. Her RECIST staging criteria showed 2% increase of lymph node size from baseline at the first restage, and 4% increase of lymph node size from baseline at the second restage.

After completing 7 cycles, the subject withdrew consent for therapy in order to try another experimental treatment. After being off study for 8 weeks, the subject physician requested that she be allowed to resume therapy with MABp1 due to "rapid disease progression". Since resuming treatment, the subject's disease is stable and she has been on study for over 58 weeks.

Example 5—Treatment of NSCLC with an IL-1α-Specific MAb (Xilonix™)

The subject was an 84 year old female with a history of metastatic non-small cell lung cancer diagnosed by fine needle aspiration. Three months after diagnosis, the subject began treatment with Tarceva® (Erlotinib) for 8 months at which point disease progression was noted. The subject was then treated with 11 cycles of Alimta® (Permetrexed) over 8 months, at which time treatment was halted due to the development of renal failure of undetermined etiology. Six months later, progressive disease was noted and the patient was again treated with Tarceva® (Erlotinib) for 3 months. At that point, her CAT scan showed further progressive disease in the lungs with an increase in size of a right upper-lobe mass, pulmonary nodules consistent with metastases, and increasing intra-thoracic adenopathy.

The subject was then enrolled in a trial using Xilonix™. MABp1 (3.75 mg/kg) was infused intravenously every 21 days for 9 cycles. After treatment, stable disease was noted for approximately 30 weeks, and in the most recent restaging the right lung lesion appeared to be cavitating.

Example 6—Treatment of Non-small Cell Lung Cancer with an IL-1α-specific MAb (Xilonix™)

The subject was a 52 yr old female diagnosed with KRAS-positive non-small cell (adenocarcinoma) cancer of the lung on day 0. A PET/CT scan from day 14 revealed a 4×3.5 cm left upper lobe mass, with disease metastasis to the lungs, hilar nodes, right inguinal nodes, right adrenal, 4th right rib, and sacroiliac joint. The subject began treatment with Carboplatin, Paclitaxel, and Bevacizumab a few weeks after the scan. The subject had a good initial response and completed five cycles before progressing at about 5 months from the first treatment. Over the next six months, the subject was treated with 3 cycles of Docetaxel and one cycle of Carboplatin plus Pemetrexed. Despite this therapy, she continued to progress.

The subject subsequently began treatment with MABp1. After only 4 days the subject began experiencing a worsening of her headaches. These were initially attributed to sinusitis, but MRI revealed brain metastases. The investigator believed that these were likely present prior to beginning therapy, however, the subject came off of study after only one dose of MABp1 to receive gamma-knife radiotherapy. The subject was seen in follow up twenty days after the initial MABp1 dose, and reported a subjective improvement in symptoms with a decrease in her chest pain. Because of this, the investigator checked a chest x-ray, which showed "an obvious decrease in the size of her lung lesions" after only one dose. A waiver was issued, and the subject resumed therapy. Forty-six days after the initial MABp1 dose, the subject underwent restaging, and had a 6% decrease in the sum total diameter of lesions as graded by RECIST criteria.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of reducing the size of a cancerous tumor in a human subject having cancer, the method comprising the step of administering to the subject a pharmaceutical composition comprising a pharmaceutically acceptable carrier and an amount of an anti-IL-1α antibody (Ab) effective to reduce the size of the cancerous tumor in the subject, wherein the size of the tumor in the subject is reduced, wherein the anti-IL-1α Ab is a monoclonal antibody (mAb), and wherein the mAb comprises a complementarity determining region of MABp1.
2. The method of claim 1, wherein the mAb is MABp1.

* * * * *